United States Patent
Brown

(10) Patent No.: US 8,303,547 B2
(45) Date of Patent: Nov. 6, 2012

(54) METHOD AND APPARATUS FOR SYRINGE INJECTION OF FLUIDS

(75) Inventor: Robert A. Brown, Fort Lauderdale, FL (US)

(73) Assignee: Relox Medical, LLC, Fort Lauderdale, FL (US)

( * ) Notice: Subject to any disclaimer, the term of this patent is extended or adjusted under 35 U.S.C. 154(b) by 94 days.

(21) Appl. No.: 12/498,500

(22) Filed: Jul. 7, 2009

(65) Prior Publication Data

US 2011/0009812 A1    Jan. 13, 2011

(51) Int. Cl.
*A61M 5/00* (2006.01)

(52) U.S. Cl. ............................ 604/207; 604/65; 604/218

(58) Field of Classification Search ............. 604/30, 604/31, 65–67, 118, 131, 151, 152, 154, 604/155, 207, 208, 19, 187, 218–238
See application file for complete search history.

(56) References Cited

U.S. PATENT DOCUMENTS

| | | | |
|---|---|---|---|
| 5,533,981 | A | 7/1996 | Mandro et al. |
| 2002/0183693 | A1* | 12/2002 | Peterson et al. ............ 604/151 |
| 2006/0280807 | A1 | 12/2006 | Rind |
| 2007/0260174 | A1* | 11/2007 | Jung et al. ............... 604/65 |
| 2008/0132844 | A1 | 6/2008 | Peterson et al. |
| 2008/0287873 | A1 | 11/2008 | Liberatore et al. |
| 2008/0306444 | A1 | 12/2008 | Brister et al. |

FOREIGN PATENT DOCUMENTS

WO    9611024    4/1996

OTHER PUBLICATIONS

International PCT Search Report and the Written Opinion of the International Searching Authority, or the Declaration, PCT/US2010/040893, 10 pages.

Gaby, A. R., Intravenous Nutrient Therapy: The 'Myers' Cocktail, Alternative Med. Review 2002 7(5):389-395, Thorne Research, Inc., Dover.

Witmeier, A. et al., W.I.L.P.S Wireless Interfacing Linear Positioning Syringe, Team ECE 402 Senior Design Project—www.studiosapuri.com/writingEE402DfinalDesignReview.pdf, Oct. 23, 2002, Purdue University, Indiana.

Lampl, Y., et al., Intravenous Administration of Magnesium Sulfate in Acute Stroke: A Randomized Double-Blind Study, Clinical Neuropharmacology, 2001 24(1):11-15 Lippincott Williams & Wilkens, Inc., Philadelphia.

(Continued)

*Primary Examiner* — Kevin C Sirmons
*Assistant Examiner* — Kami A Bosworth
(74) *Attorney, Agent, or Firm* — Fredrikson & Byron, P.A.

(57) ABSTRACT

A system for delivering or withdrawing a fluid to or from the body of a patient in a manner that permits delivery to be controlled based upon feedback from the patient, the system including a syringe assembly providing a syringe operably coupled to one or more sensors adapted to determine one or more corresponding parameters associated with fluid delivery and/or withdrawal, and a monitor adapted to be communicably associated with the one or more sensors of the syringe assembly, and optionally with other sensors or inputs providing additional parameters as well, the monitor comprising one or more read out mechanisms either directly or indirectly corresponding to the one or more fluid delivery/withdrawal parameters, and optionally with one or more of the additional parameters as well.

20 Claims, 7 Drawing Sheets

OTHER PUBLICATIONS

Muir, K. W., et al., Magnesium for acute stroke (Intravenous Magnesium Efficacy in Stroke trial): randomised controlled trial, The Lancet, Feb. 7, 2004 363(9407):439-445.

Lees, K. R., et al., New experimental and clinical data on the efficacy of pharmacological magnesium infusions in cerebral infarcts, Magnesium Research, 1998 11(1):43-56, John Libbey Eurotext Limited, Le Pecq, France.

Rusyniak, D. E., et al., Hyperbaric Oxygen Therapy in Acute Ischemic Stroke: Results of the Hyperbaric Oxygen in Acute Ischemic Stroke Trial Pilot Study, Stroke, published online Jan. 16, 2003, 34:571-574, American Heart Association, Dallas.

Saver, J. L., et al., Prehospital Neuroprotective Therapy for Acute Stroke: Results of the Field Administration of Stroke Therapy-Magnesium (FAST-MAG) Pilot Trial, Stroke, published online Mar. 11, 2004, 35:e106-e108, American Heart Association, Dallas.

Schouten, J. W., Neuroprotection in traumatic brain injury: a complex struggle against the biology of nature, Current Opinion in Critical Care 2007 13:134-142, Lippincott Williams & Wilkins, Philadelphia.

Temkin, N. R., et al., Magnesium sulfate for neuroprotection after traumatic brain injury: a randomised controlled trial, The Lancet Neurology, published online Nov. 30, 2006, 6(1):29-38.

Muir, K. W., et al., A Randomized, Double-Blind, Placebo-Controlled Pilot Trial of Intravenous Magnesium Sulfate in Acute Stroke, Stroke, published online http://stroke.ahajournals.org/cgi/content/full/26/7/1183 1995 26:1183-1188. American Heart Association, Dallas.

Vink, Robert et al., Magnesium in acute and chronic brain injury: an update, Magnesium Research. vol. 22, No. 3, 158-62, Sep. 2009, 12th International Magnesium Symposium.

\* cited by examiner

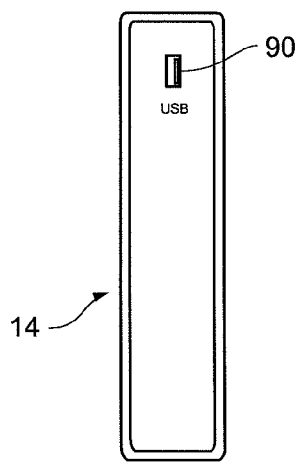
Fig. 6B
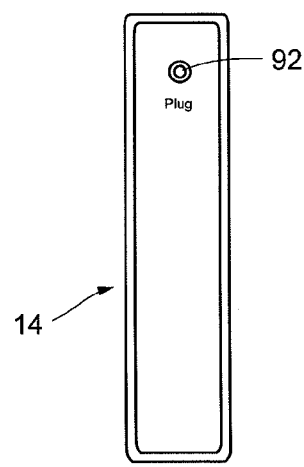
Fig. 6C
Fig. 6D
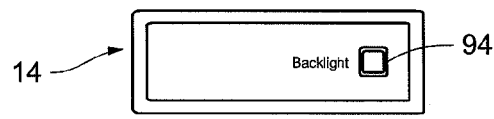
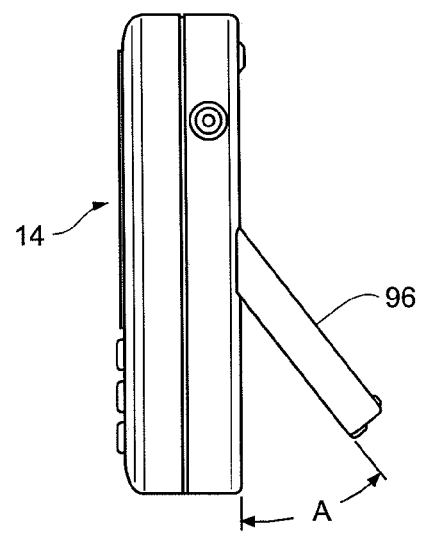
Fig. 7

METHOD AND APPARATUS FOR SYRINGE INJECTION OF FLUIDS

TECHNICAL FIELD

The present invention relates to methods and corresponding syringe mechanisms for use in delivering and/or withdrawing fluids to and/or from the body.

BACKGROUND OF THE INVENTION

Syringes have long been used to deliver fluids to the body. Standard approaches in the use of syringes include those that are prefilled with the material (generally solution) to be delivered. Syringes have been described that are capable of manual operation, as well as those that employ automated operation, e.g., on a timed or continual infusion approach.

On a related subject, Applicant has itself developed a method for the treatment of diseases such as stroke. See, for instance, US Publication No. 2006/0280807 (Rind).

SUMMARY OF THE INVENTION

The present invention provides a system for delivering or withdrawing a fluid to or from the body of a patient in a manner that permits delivery to be controlled based upon feedback from the patient, the system including:

a) a syringe assembly comprising a syringe adapted to contain, and to deliver and/or withdraw, a fluid to and/or from the body, the syringe being operably coupled to one or more sensors adapted to determine one or more corresponding parameters associated with fluid delivery and/or withdrawal, and b) a monitor adapted to be communicably associated with the one or more sensors of the syringe assembly, and optionally with other sensors or inputs providing additional parameters as well, the monitor comprising one or more read out mechanisms (e.g., visual or auditory displays or signals) either directly or indirectly corresponding to the one or more fluid delivery/withdrawal parameters, and optionally with one or more of the additional parameters as well.

The system can be used, for instance, to deliver fluid (e.g., drug or other solution) to the patient in a manner that can be controlled based, in whole or in part, manually by the infusionist, and upon feedback from the patient. Such feedback can be of any suitable type, e.g., an indication made directly or indirectly by the patient him or herself, and/or it can be based upon one or more parameters determined by the use of corresponding sensors.

Such patient indications can be based upon any suitable criteria, e.g., pain, temperature sensation, dizziness, movement, or other physical manifestation. The indication itself can be provided in any suitable manner, e.g., as a physical or oral indication, or by actuation of a suitable indicator means (e.g., hand-controlled button or switch). In turn, the indication can be binary (e.g., yes or no) or it can be qualified or quantified in some manner (e.g., as an indication of a position along a scale or continuum).

In turn, the parameters determined by the one or more sensors can also be related to either the patient response (e.g., blood pressure, temperature), or to delivery parameters relating to the fluid delivered or withdrawn (e.g., rate, amount), or both.

In a particularly preferred embodiment, the delivery can be manually or semi-manually controlled based upon one or more patient indicators selected from the group consisting of thermal sensation, pain, or other physical sensation (e.g., dizziness). The system preferably also includes associated processors, soft- or firmware and displays related to measurements being taken from the patient related to the infusion or withdrawal, and providing safety and/or efficacy, and/or biological data such as temperature, oxygen saturation, respiratory rate, blood pressure, pressure at the site of the infusion (e.g., to assess extravasation), and heart rate.

The method and system of the present invention can be used for the delivery of any material (e.g., solution) to a patient where such delivery (e.g., by infusion) is given and where control of the rate is desirable or required, and enhanced safety may result. In turn, the system of this invention is particularly well suited for use with the delivery of solutions for the treatment or prevention of various diseases, conditions, syndromes, or disorders, such as stroke and ischemia, where delivery is preferably controlled based upon an indication of temperature sensation by the patient. See, US Publication No. 2006/0280807 (Rind), the disclosure of which is incorporated herein by reference.

In one preferred embodiment, the parameters are selected from the group consisting of the total amount delivered over time, the rate of injection, and one or more corresponding safety ranges or indicators (e.g., yes/no indications), optionally and preferably in combination with other measurements related to the functions and requirements associated with safety considerations, and patient monitoring related to the infusion.

Optionally, and preferably, the system also provides one or more features selected from the group consisting of memory functions, data storage capability, printout capability, download to a computer, calibration, fail safe mechanisms, power indicator, reset function, and alarm notification.

In a preferred embodiment, a syringe assembly of this invention comprises: a) a syringe comprising a barrel, plunger and needle adapted to contain and deliver a fluid, and b) one or more sensors directly or indirectly associated with the syringe assembly and corresponding to one or more respective delivery/withdrawal parameters. Such delivery/withdrawal parameters can include any parameter of relevance or potential relevance to the patient or provider, or both, including those selected from the group consisting of:

Rate of fluid delivery or withdrawal

Amount of fluid delivered or withdrawn at any point in time and/or in total

Amount of drug or material delivered or withdrawn at any point in time and/or in total Concentration of drug or material being delivered (e.g., mg/ml)

Pressure of fluid delivery or withdrawal

Velocity of the fluid delivered or withdrawn

Time associated with fluid delivery or withdrawal

Size of the syringe being used

Amount of fluid in the syringe being used

Memory capacity of the information being stored and the amount used

Temperature of the fluid and/or patient

Tissue (e.g., blood) levels of one or more analytes (e.g., oxygen, ATP)

The parameters can be selected and in turn determined and used in any suitable manner, e.g., on their own or in combination with other parameters, and in one or more relationships (e.g., the delivery rate as compared to patient temperature).

The sensors can be of any suitable type, e.g., mechanical, electromagnetic, optical, pneumatic, hydraulic, photosensitive sensors, flow meter types, pressure types, Doppler sensing types, imbedded magnets in the head of the plunger, and variations thereof. In turn, the sensors can be used to determine parameters in any suitable manner, e.g., by automated analysis and/or mechanical or other suitable actuation.

A primary sensor can be associated with the syringe assembly in any suitable manner, e.g., with the barrel, plunger and/or needle components of the syringe. In turn, a sensor can be coupled to or with the syringe in any suitable relationship, e.g., with the sensor upon, within, around, adjacent, or integral with one or more syringe components. In one embodiment, one or more sensors and syringe control features are associated with an aftermarket device that can be coupled together with a conventional syringe or connected to the monitor. In yet another embodiment, one or more sensors and/or syringe control features can be incorporated or built into one or more components of the syringe itself In turn, the syringe assembly can be used in any suitable manner, e.g., manual (human powered infusion), automated, and combinations thereof. The syringe itself can be made of any suitable material, e.g., glass, plastic or other materials, and can be either reusable or disposable in whole or in part, and can be provided with conventional connections (e.g., LUER-LOK™ tip, slip-tip, or eccentric tips). In turn, the syringe can be provided in any suitable size, e.g., from 1 cc to 200 cc. The syringe needle can itself be detachable, retractable or permanently attached, and the needle the syringe can itself be remote from the needle of the syringe, as in a butterfly configuration. The syringe assembly, including portions of the syringe and corresponding sensors, can be provided in sterile form where necessary, and in either single use (e.g., disposable) or reusable form.

For instance, the system can be operated using manual and/or automatic control of any or all aspects, including for instance, feedback from the sensor to the infusionist. Automatic control can include, for instance, automatic feedback of information by a flashing light or sound, as an alarm from the monitor, e.g., if a certain rate of infusion is exceeded, and/or automatic control of the injection per se. Such options include manual and/or automated (including semi-automated, e.g., in which certain aspects remain subject to manual control) of the feedback from the sensor to the infusionist.

The operable connection between any aspect of the invention, e.g., between the syringe or its sensors (and the monitor), can be in any suitable form, e.g., manual, mechanical, electrical or other such connection, or wireless.

In a particularly preferred embodiment, the apparatus of this invention is used for intravenous administration, but can be used for all types of injections, including other forms of parenteral injections, such as sub-cutaneous, intra-muscular, intra-arterial, intradermal, and the like.

An apparatus of this invention further provides a monitor adapted to be communicably connected to the one or more sensors associated with the syringe assembly, the monitor comprising one or more displays either directly or indirectly corresponding to the one or more parameters.

Optional features of the monitor include, but are not limited to one or more corresponding memory functions, data storage and printout capabilities, connection to a computer, calibration and reproducibility features, fail safe mechanisms, thermal (e.g., warmth or coolness) indicators, name of patient, memory capacity and amount used, time of day, time of injection, size of syringe being used, amount of fluid in the syringe, sensation indicators, temperature indicators, as well as reset control, power indicator, and additional information, indicators, ranges, scales (e.g., dizziness).

In a preferred embodiment, the system further provides a solution to be delivered using the syringe mechanism and module of this invention. Suitable fluids are those that benefit from a predictable or controllable delivery, examples of which include, but are not limited to those solutions designed to elicit an immediate response on the part of the patient, e.g., in terms of pain alleviation, anesthesia, or thermal sensation.

In a particularly preferred example, the system of this invention is used to practice a method for treating, preventing, and/or diagnosing (e.g., contrast media) disorders such as stroke, cerebral palsy and brain/head trauma and other injuries. In addition, the method is useful for treating patients after surgery to speed healing and recovery by administering a solution containing certain ions and nutrients to a patient, preferably while the patient is breathing pure or nearly pure oxygen or a mixture of gases having greater than about 20% oxygen. The methods of the invention can also be used to promote healing of damaged tissue, for example, damaged muscle tissue. The method is useful for tissue damage or disease caused by any of a wide variety of factors, including, genetic problems, environmental problems, bruising, ischemia-reperfusion injury, infection, and inflammation.

In such a preferred embodiment, the apparatus can be used in a method for treating a patient comprising: (a) injecting into the bloodstream of a patient is breathing a gas mixture having greater than about 20% oxygen, and more preferably greater than about 25% oxygen, an aqueous solution comprising about 0.1 to about 1 M Mg++ and having an osmolarity less than about 1500 mOSm/l; and (b) increasing the rate of injection at least until the patient feels a sensation of warmth. In some embodiments, the method entails treating a region of the body of a patient and increasing the rate of injection at least until the patient feels a sensation of warmth in the region of the body to be treated. In some embodiments the patient provides feedback regarding the sensation of warmth so that a sensation of warmth in the target area can be achieved and/or maintained for a desired period of time. In some embodiments are temperature measuring device (e.g., a infrared temperature measuring device) is used to monitor increase in warmth of a target area of the patient's body. In some embodiments the rate of administration of the solution is varied based on feedback from the patient and/or measurements made by the temperature measurement device.

In various embodiments: the patient is administered a breathing mixture comprising at least 40% oxygen; the patient is administered a breathing mixture comprising at least 60% oxygen; the patient is administered a breathing mixture comprising at least 90% oxygen; the breathing mixture includes at least about 0.5% $CO_2$; the breathing mixture includes about 0.5% to about 10% (and more preferably, about 1% to about 6%) $CO_2$; breathing mixture is administered to the patient at greater than normal atmospheric pressure; the rate of injection is increased until the patient feels a sensation of warmth in a part of the body in need of treatment; the rate of injection is not substantially increased after the patient feels a sensation of warmth; the rate of injection varied to maintain the sensation of warmth for a desired period of time; the total amount of solution administered in one treatment session is between 0.5 ml/kg and 2 ml/kg of patient body weight; the average rate of injection is greater than 0.1 ml/sec; the osmolarity of the solution is less than 1200 mOsm/L; osmolarity of the solution is less than 1100 mOsm/L; the osmolarity of the solution is less than 1000 mOsm/L; the osmolarity of the solution is less than 900 mOsm/L; the osmolarity of the solution is between 200 and 1100 mOsm/L; the solution contains up to 6 mg/ml ascorbic acid; the solution contains 0.1 to 0.7 M (0.1 to 0.6 M, 01 to 0.5 M; 0.15 M to 0.6 M; 0.15 to 0.35 M) magnesium chloride; the solution contains 0.1 to 0.7 M (0.1 to 0.6 M, 01 to 0.5 M; 0.15 M to 0.6 M; 0.15 to 0.35 M) magnesium sulfate; the solution contains 0.1 to 0.7 M (0.1 to 0.6 M, 01 to 0.5 M; 0.15

M to 0.6 M; 0.15 to 0.35 M) Mg2+ ions; the patient has suffered a stroke, brain injury, cerebral palsy, viral or chemical injury to the brain; the solution contains one or more of vitamin B12, vitamin B6 and vitamin B5; the solution contains vitamin B12, vitamin B6 and vitamin B5; the solution contains less than 1% by weight calcium gluconate; the solution does not contain calcium gluconate; the solution contain less than 0.001 M Ca2+; the breathing mixture is administered through a masking covering the patient's nose and mouth, which masked is sealed to substantially prevent leakage of the breathing mixture; the patient is reclining during treatment; the patient has consumed at least 200 calories within 3 hours prior to treatment; and the patient consumed or has been administered at least 2 ml/kg body weight of water within 3 hours prior to treatment.

The methods of the invention, which entail administration of a healing solution containing magnesium ions and additional optional components, can promote more rapid healing of brain injury or other physical trauma than can be achieved without treatment or with only physical therapy. The healing solution administered in the method of the invention has a relatively high level of magnesium ions, at least compared to many commonly used intravenous solutions, and is formulated so as permit the healing solution to be safely and comfortably administered to the patient intravenously at a relatively rapid rate. Thus, the osmolarity and the pH of the solution are set relatively close to physiological levels found in blood.

The healing solution can contain a variety of components in addition to magnesium ions. For example it can contain vitamin C. In some cases, bicarbonate or some other base or a buffer is require to reduce the acidity of solutions containing vitamin C. The healing solution can contain calcium gluconate, but in many cases it is desirable to reduce or eliminate calcium gluconate, particularly where it is desirable to increase the vasodilatory effect of the solution. The healing solution can contain various vitamins, particularly B vitamins, and micronutrients. The healing solution can also include a buffer even where vitamin C is not present.

The healing solution should be injected directly into a vein and should be administered while the patient is breathing a gas mixture that is enriched in oxygen compared to normal air, for example a gas mixture that is greater than 25% (30%, 40%, 50%, 60%, 70%, 80%, 90%) oxygen. In many cases it is desirable to have the patient breath 99-100% oxygen, preferably through a close fitting mask covering the mouth and nose (and preferably sealed to prevent leakage using tape or some other sealant) or through an endotracheal tube. The gas mixture or oxygen is preferably administered at or greater than atmospheric pressure, e.g., at a high flow rate or via a pressure bag. Alternatively, the healing solution can be administered to the patient while the patient is in a hyperbaric chamber and breathing a mixture of gasses having at least 25% (30%, 40%, 50%, 60%, 70%, 80%, 90%, 100%) oxygen.

In yet another embodiment, the present invention provides a kit, comprising a syringe assembly and/or monitor as described herein, in combination with a solution to be delivered, and optionally, in combination with one or more components selected from the group selected from: a) a face mask to permit the delivery of respirable gas in the course of use, b) a computer adapted to interface with the syringe assembly. In a related manner, the invention provides a syringe assembly (including sensor or syringe thereof), or monitor adapted to be used in the preparation and/or use of a system of this invention.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 6B is a side view of the monitor of FIG. 6A.

FIG. 6C is a side view of the monitor of FIG. 6A.

FIG. 6D is a top view of the monitor of FIG. 6A.

FIG. 7 is a side view of a monitor including a stand according to an embodiment of the invention.

DETAILED DESCRIPTION

Figure 1:
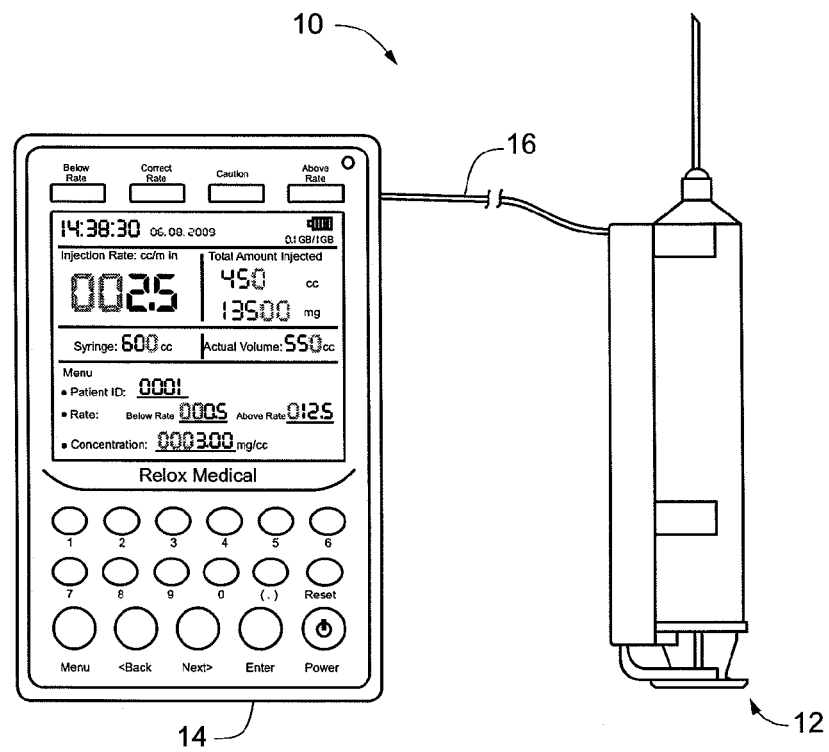
FIG. 1 illustrates a system for use in delivering and/or withdrawing fluids to and/or from the body according to an embodiment of the invention.

In one preferred embodiment, the system includes a syringe assembly and monitor as shown in FIGS. 1-7. FIG. 1 illustrates a system 10 for use in delivering and/or withdrawing fluids to and/or from the body according to an embodiment of the invention. In certain embodiments, the system 10 includes a syringe assembly 12 and a monitor 14 coupled by a communication link 16. Briefly, in certain embodiments the syringe assembly 12 is adapted to contain and deliver and/or recover a fluid to and/or from the body. The syringe assembly 12 includes one or more delivery and/or recovery sensors that determine one or more corresponding parameters associated with fluid delivery and/or recovery. The monitor communicates with the one or more sensors of the syringe assembly 12 via the communication link 16. For example, the monitor 14 and the syringe assembly 12 can be coupled with a link 16 comprising a wired or a wireless link. The monitor 14 includes one or more read out mechanisms (e.g., visual or auditory displays or signals) that correspond (directly or indirectly) to the one or more parameters.

In certain embodiments the system can be used, for instance, to deliver fluid to the patient in a manner that can be controlled based, in whole or in part, upon feedback from the patient. Such feedback can be of any suitable type, e.g., an indication made directly or indirectly by the patient him or herself, and/or it can be based upon one or more parameters determined by the use of corresponding sensors, including for example, a visual and/or audible reference to one or more measured parameters.

Figure 2A:
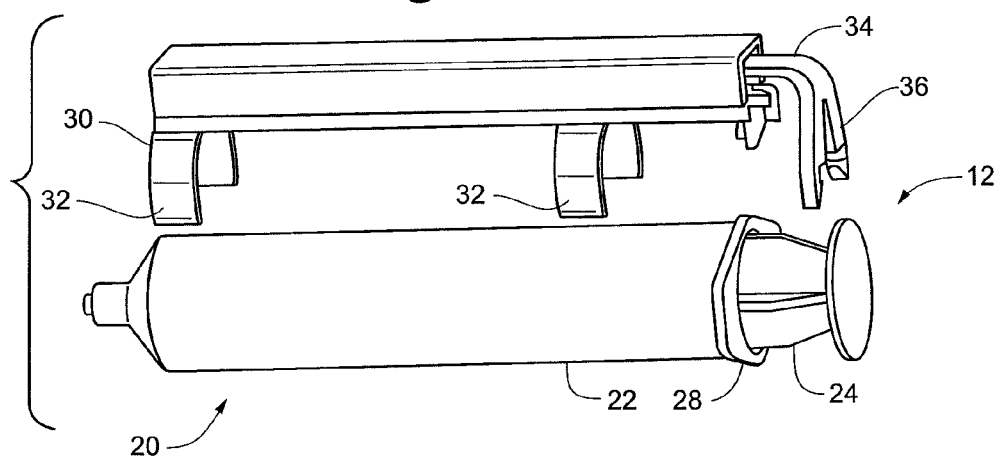
FIG. 2A is a perspective view of a syringe assembly according to an embodiment of the invention.

FIG. 2A is a perspective view of a syringe assembly 12 according to certain embodiments of the invention. The syringe assembly 12 preferably comprises a syringe 20 and a sensor 30, which can be coupled together in various fashions depending upon the desired design. For example, as shown in the figures throughout, the syringe assembly 12 can comprise a typical type of syringe and a separate sensor (e.g., a custom or an aftermarket sensor device) that couples to the syringe. In certain embodiments, though, the sensor 30 may be integral with the syringe 20 instead of being formed as a separate, coupled device.

In a preferred embodiment, the syringe 20 includes a barrel 22 defining a flange 28, a plunger 24, and a needle 26 (shown in FIG. 2B) and the sensor 30 can be coupled with the syringe 20 in any suitable manner, e.g., with the barrel, plunger and/or needle components of the syringe. The syringe 20 can be made of any suitable material, e.g., glass, plastic or other materials, and can be either reusable or disposable in whole or in part, and can be provided with conventional connections (e.g., LUER-LOK™ tip, slip-tip, or eccentric tips). In turn, the syringe 20 can be provided in any suitable size, e.g., from 1 cc to 200 cc. The syringe needle 26 can itself be detachable, retractable or permanently attached, and the needle 26 of the syringe can itself be remote from the syringe, as in a butterfly configuration. The syringe assembly 12, including portions of the syringe 20 and corresponding sensors 30, can be provided in sterile form where necessary, and in either single use or reusable form.

In certain embodiments, the sensor 30 includes a sensor plunger 34 adapted to couple with the plunger 24 of the syringe 20. The sensor 30 further includes a sensing device associated with the sensor plunger 34, for sensing parameters related to the functioning of the syringe assembly 12 in any infusion or exfusion application and communicating the parameters to the monitor, more of which will be discussed further herein.

Figure 2B:
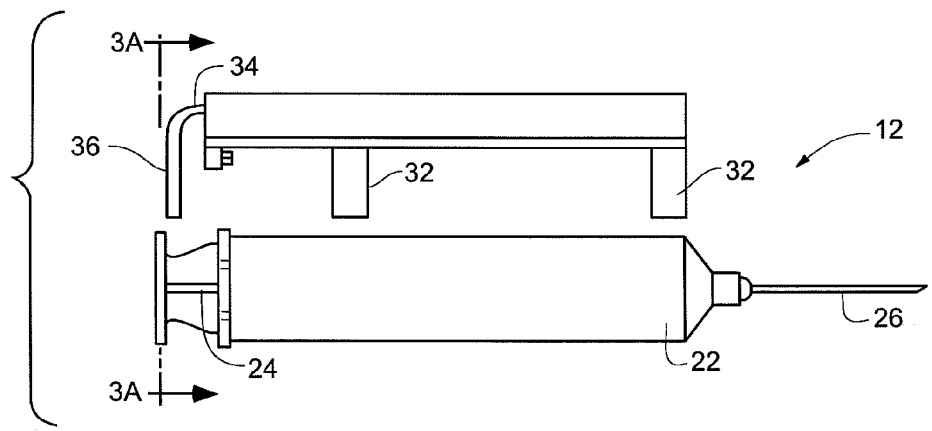
FIG. 2B illustrates a syringe assembly showing the separation of a sensor and a syringe according to an embodiment of the invention.
Figure 2C:
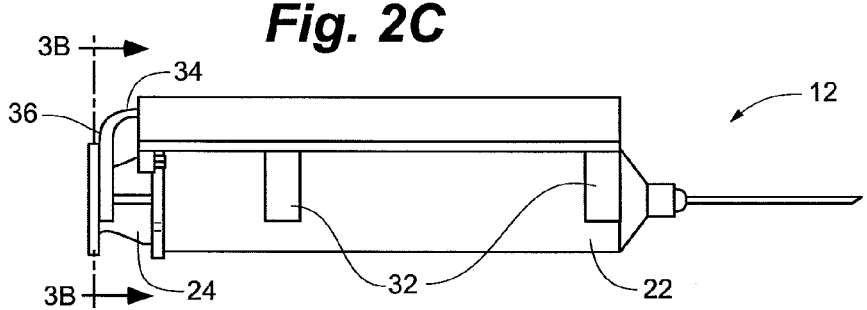
FIG. 2C illustrates the syringe assembly of FIG. 2B, wherein the sensor and syringe are fastened together according to an embodiment of the invention.

In cases in which the sensor 30 is a separate component from the syringe 20, the sensor 30 and/or syringe 20 can include one or more features that couple and/or lock the syringe 20 and the sensor 30 together. In some embodiments the coupling and/or lock can include a removable and/or semi-permanent style of coupling allowing the syringe 20 and sensor 30 to be separated. In certain embodiments the coupling results in a more permanent fastening of the syringe and sensor. For example, returning to FIG. 2A, in some embodiments the sensor 30 can include one, two, or more fasteners 32 that couple the sensor 30 to the barrel 22 of the syringe 20. The fasteners 32 can take a wide variety of forms. In the illustrated embodiment, for example, the fasteners 32 comprise plastic, resilient partial rings that slip onto the syringe barrel 22. FIG. 2A shows an additional feature for coupling and/or locking the sensor 30 with the syringe 20. For instance, the sensor plunger 34 can have a lock 36 formed at an end of the sensor plunger 34, thus allowing the sensor plunger 34 to couple with the plunger 24 of the syringe. FIGS. 2B and 2C show views of the syringe assembly 12 respectively before and after assembly, according to embodiments of the invention.

Figure 3A:
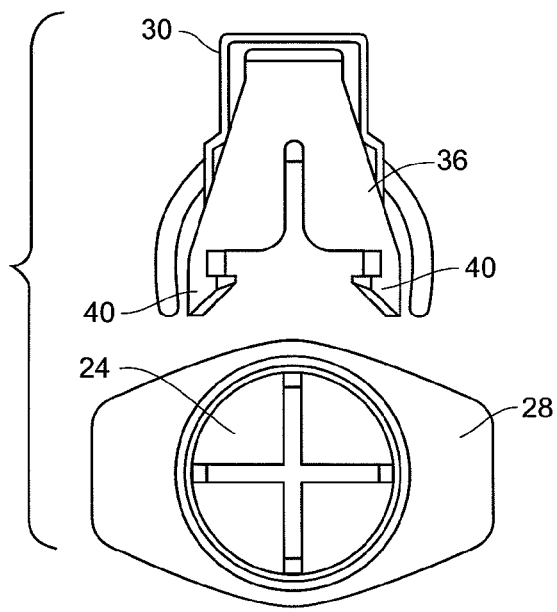
FIG. 3A is a cross-section of FIG. 2B, taken along line 3A.
Figure 3B:
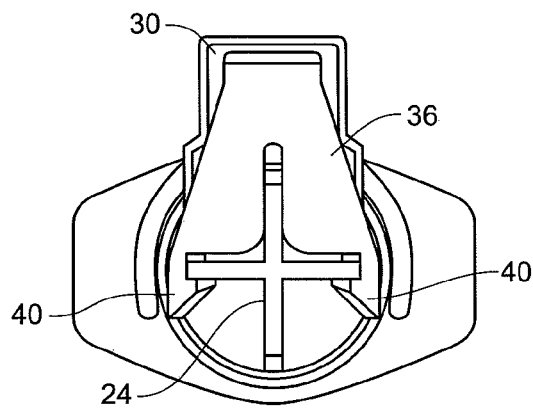
FIG. 3B is a cross-section of FIG. 2C, taken along line 3B.
Figure 3C:
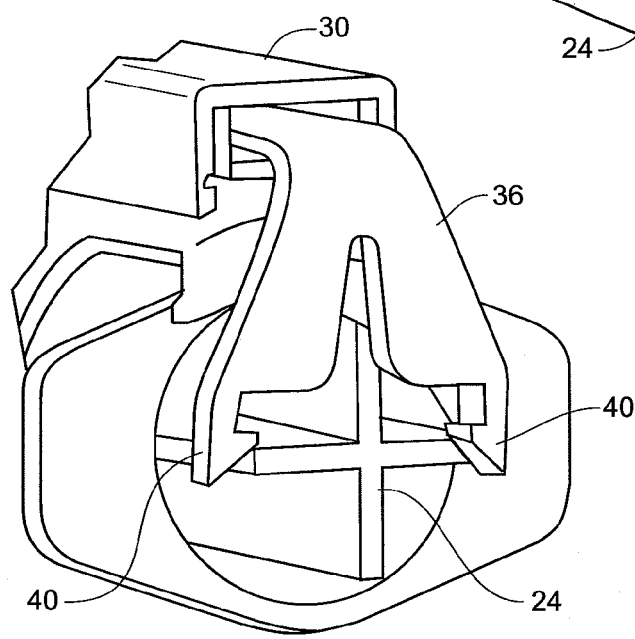
FIG. 3C is a perspective view of the end of a syringe assembly according to an embodiment of the invention.

FIG. 3A is a cross-section of FIG. 2B, taken along line 3A, illustrating the lock 36 in greater detail before the sensor plunger 34 and the syringe 20 are coupled together. FIG. 3B is a cross-section of FIG. 2C, taken along line 3B, illustrating the lock 36 after the syringe 20 and the sensor plunger 34 are coupled together. As shown in FIGS. 2A-2C, the lock 36 can be formed at the end of the sensor plunger 34 and adapted to couple with the syringe plunger 24. The design of the lock 36 is not fixed, but is preferably formed to engage with the plunger 24 according to the design and shape of the plunger 24. For example, in the illustrated embodiment, the lock 36 includes a generally cross-shaped relief that is adapted to engage with the cross-shaped shaft of the syringe plunger 24. In certain embodiments, the lock 36 includes one or more clips 40 that engage with the syringe plunger to lock the sensor plunger 34 and the syringe plunger 24 together (e.g., semi-permanently or permanently). FIG. 3C is a perspective view of the end of a syringe assembly 12 showing a partial engagement of the lock 36 with the syringe plunger 24. The lock 36 and/or clips 40 can be formed of a somewhat resilient material, allowing the clips 40 to flex as the sensor plunger 34 is mounted to the syringe plunger 24 and the clips engage the syringe plunger 24.

Figure 4A:
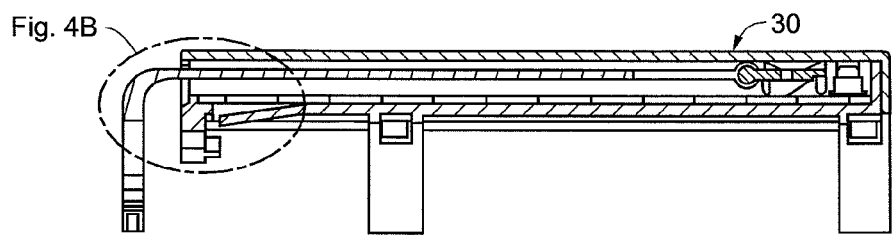
FIG. 4A is a longitudinal cross-section of a sensor according to an embodiment of the invention.
Figure 4B:
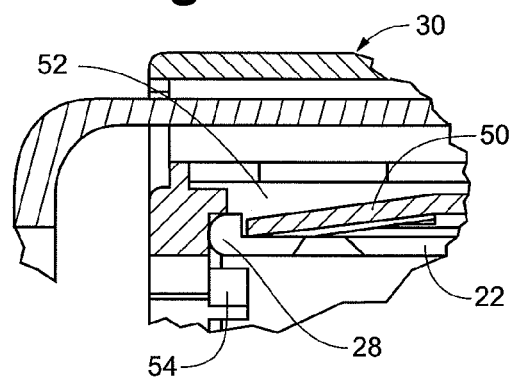
FIG. 4B is an exploded view of portion 4B of FIG. 4A, including a partial cross-section of a syringe according to an embodiment of the invention.
Figure 4C:
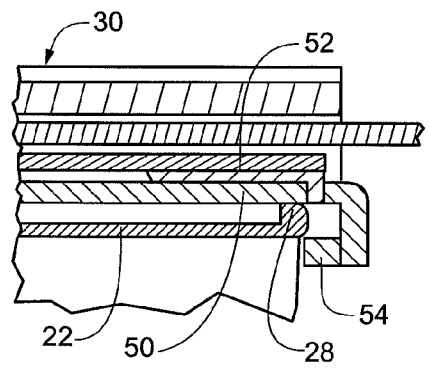
FIG. 4C is a partial cross-section of a syringe assembly illustrating a flip lock in a first position according to an embodiment of the invention.
Figure 4D:
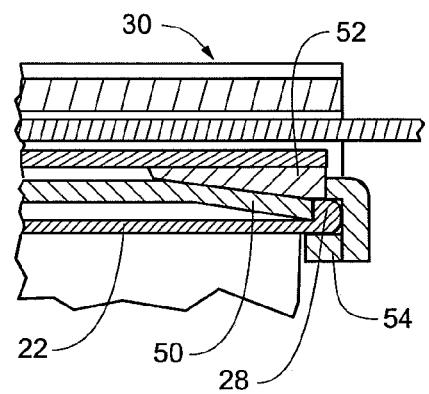
FIG. 4D is a partial cross-section of the syringe assembly of FIG. 4C illustrating the flip lock in a second position according to an embodiment of the invention.

FIGS. 4A-4D illustrate another type of lock or fastener that can couple the syringe 20 and the sensor 30 of the syringe assembly. FIG. 4A is a longitudinal cross-section of the sensor 30 according to certain embodiments, and FIG. 4B is an exploded view of portion 4B of FIG. 4A, with the addition of a partial view of a syringe. As shown in FIG. 4B, the sensor 30 is positioned proximate the barrel 22 and flange 28 of the syringe. According to certain embodiments, the sensor 30 includes a flip-lock 50 adapted to engage the syringe barrel 22 and flange 28. The sensor 30 can also include a lock hook 54 adapted to receive the flange 28 of the syringe. In certain embodiments, the sensor 30 may include a resilient member 52 (e.g., a material with a spring constant) that urges the flip-lock 50 into engagement with the syringe once the syringe is properly positioned adjacent the sensor. Turning to FIG. 4C for example, the flip-lock 50 can move inwards (e.g., optionally against the spring constant of the optional resilient member 52) as the syringe 20 and sensor 30 are brought together, thus providing a clear path for engagement. Turning to FIG. 4D, as the flange 28 of the syringe is received within the lock hook 54, the flip-lock 50 is urged into frictional engagement with the syringe barrel 22 and flange 28. Accordingly, the flip-lock 50 can provide a manner of coupling and/or locking together the syringe and sensor of the syringe assembly in a preferred embodiment.

Figure 5:
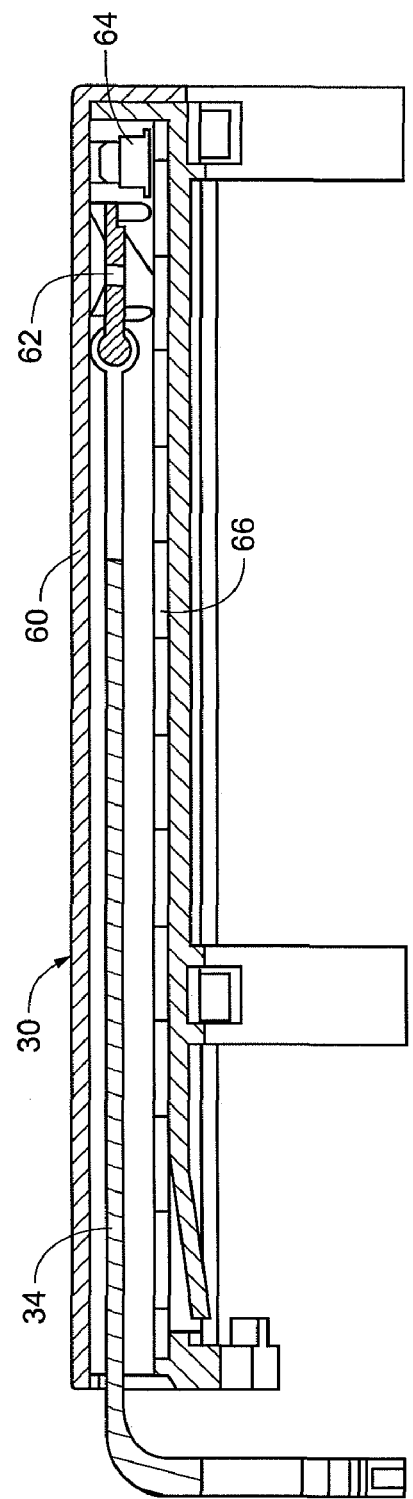
FIG. 5 is a longitudinal cross-section of a sensor according to an embodiment of the invention.

Turning to FIG. 5, a longitudinal cross-section of a sensor 30 is illustrated according to an embodiment of the invention. Briefly, the sensor 30 includes a housing 60 and the sensor plunger 34 that is movably received and coupled in the housing 60. The housing also includes a sensor device, substrate, or chip 62 (individually or collectively sometimes referred to as a sensor "chip" or "chips") that is operably coupled with the sensor plunger 34. For example, in some embodiments as the sensor plunger 34 passes through the sensor chip 62, the sensor chip 62 detects a change in the voltage of a printed or otherwise deposited circuit board or other substrate 66 positioned within the housing 60. The sensor chip 62 notes the voltage change and outputs a corresponding signal to the monitor in a preferred embodiment. The sensor 30 can further include a plug 64, coupled with the sensor chip 62, adapted to receive a cable or wired communication link to connect the sensor 30 with the monitor.

The sensor chips can be of any suitable type, e.g., mechanical, electromagnetic, optical, pneumatic, hydraulic, photo-sensitive sensors, flow meter types, pressure types, piezoelectric, Doppler sensing types, imbedded magnets in the head of the plunger, and variations thereof. In turn, the sensor 30 can be used to determine parameters in any suitable manner, e.g., by automated analysis and/or mechanical, hydraulic or other suitable actuation.

Figure 6A:
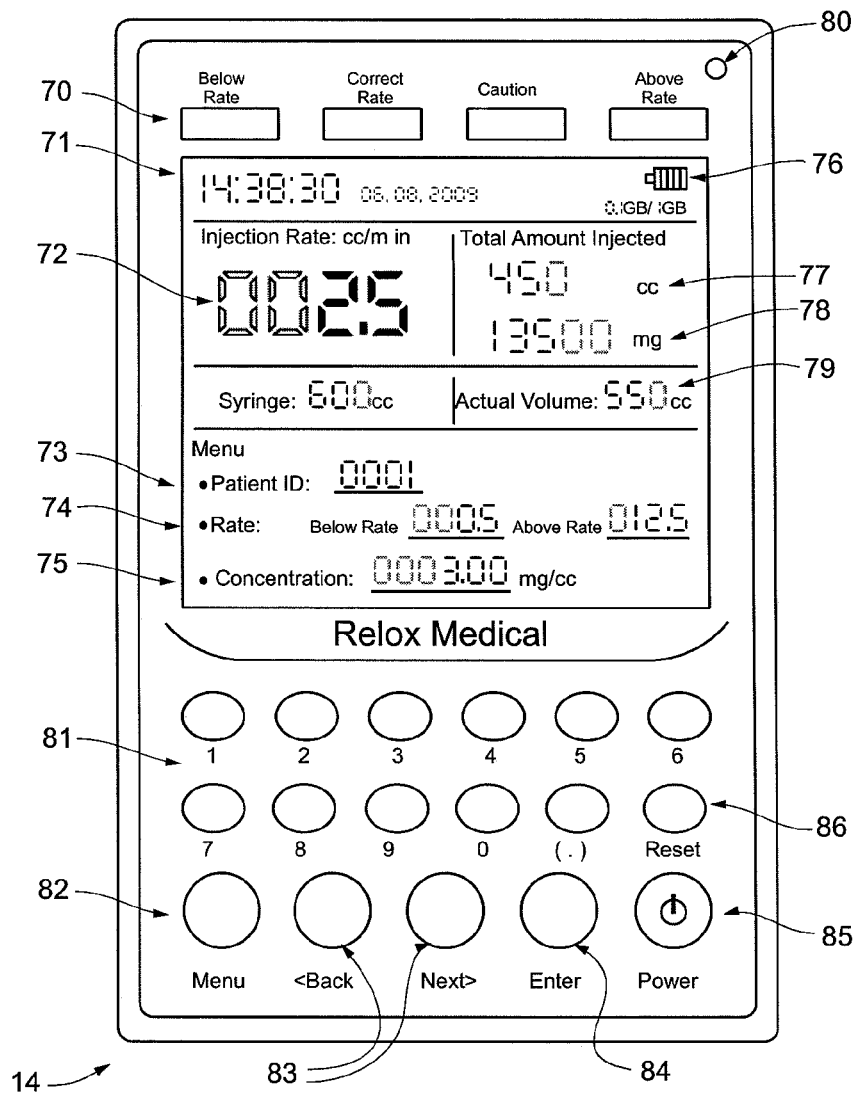
FIG. 6A is a front view of a monitor according to an embodiment of the invention.

Turning to FIG. 6A, a front view of a monitor 14 is shown according to one preferred embodiment of the invention. In a preferred embodiment, the monitor 14 includes a number of keys and a variety of displays adapted to display one or more values corresponding (directly or indirectly) to one or more parameters. According to certain embodiments, the displayed values and/or parameters can be selected from the group consisting of, but not limited in either number or function, the total amount of infusate delivered over a defined period of time, the rate of injection over a defined period of time, and one or more corresponding safety ranges or indicators (e.g., yes/no indications). Optional features of the monitor 14 include, but are not limited to, one or more corresponding memory functions, data storage and printout capabilities, computer outputs, calibration and reproducibility features, fail safe mechanisms, thermal (e.g., warmth or coolness) indicators, sensation indicators, temperature indicators, as well as reset control, power indicator, and additional information, indicators, ranges, scales (e.g., for dizziness).

For example, as shown in FIG. 6A, the monitor 14 can include features including, but not limited to:

A rate alarm 70, including, for example, four color-flash rate indications/zones customizable by a user. One example of rate zones and alarms include: Below Rate—White, Correct Rate—Green, Caution Rate—Yellow, Above Rate—Red.

A time display 71 that displays the current date and time, precise to the second for example. The time can be set by continually pressing the menu key for 3 seconds.

An injection rate 72 that is able to, for example, accurately display the injection speed.

A patient ID input 73 which allows a user to input and display an ID for every patient.

A rate reset display 74 that allows the rate to be set and displayed.

A concentration display 75 displaying the corresponding concentration.

A memory capacity display 76 that displays the used capacity versus total capacity of onboard memory.

An injected liquid display 77 that displays an automatically calculated volume of liquid that has been infused.

A total amount injected display 78 which displays a total amount injected (mg) calculated automatically based on a given "Concentration".

An indicator 79 of the total amount delivered (in cc).

An alarm indicator 80, including a red LED flashing until the "Reset" key is pressed for "Actual Volume."

A keypad 81 for the input of various alphanumeric characters.

A menu key 82.

Direction keys 83 that allow a user to choose or change one or more of the parameters.

An enter key 84.

A power key 85.

A reset key 86 that when pressed after setting all desired parameters initiates an automatic detection of the actual volume and begins a recording.

Means (not shown) for recording and/or marking data or other information relating to the procedure.

FIGS. 6B-6D illustrate various views of the monitor 14 of FIG. 6A. For example, FIG. 6B illustrates a side view of the monitor 14 showing the inclusion of a computer connection 90 that allows the monitor 14 to be coupled with a computer. FIG. 6C illustrates an additional side view of the monitor 14 including a plug 92 that allows the monitor to be coupled to the syringe assembly via the communication link as shown in FIG. 1. FIG. 6D is a top view of the monitor 14, showing a backlight key 94. Turning to FIG. 7, in some embodiments the monitor 14 further includes a stand 96 that allows the monitor 14 to be set upon a work surface, etc. For example, the stand 96 may allow the monitor 14 to recline at an angle A that may be in one embodiment about 30 degrees. Optionally, a hook (not shown) can be included at the top of the monitor in order to permit it to be hung on an IV or other pole or support.

The invention claimed is:

1. A system for delivering a fluid to the body of a patient by an infusionist, the system comprising:
    a) a syringe assembly comprising a syringe having a needle, barrel and plunger that provides for human powered infusion by manual operation of the plunger and that is adapted to contain, and to deliver a fluid to the body, the syringe plunger and barrel being coupled to one or more sensors adapted to determine flow parameters comprising the rate of fluid delivery, the amount of fluid delivered at any point in time, and the time associated with fluid delivery, and
    b) a monitor adapted to be communicably associated with the one or more sensors of the syringe assembly, the monitor comprising one or more read out mechanisms, including indicators and/or ranges, either directly or indirectly corresponding to the rate of fluid delivery, the amount of fluid delivered, and the time associated with fluid delivery, in order to provide feedback to the infusionist, and
    wherein the fluid delivery is adapted to be controlled by the infusionist based upon the parameters consisting of the rate of fluid delivery, the amount of fluid delivered, and the fluid delivery time.

2. A system according to claim 1, wherein the system comprises one or more additional sensors or inputs, not operably coupled to the syringe assembly but providing corresponding additional parameters that are communicably associated with the monitor.

3. A system according to claim 2, wherein the additional parameters comprise biological data selected from the group consisting of temperature, oxygen saturation, respiratory rate, blood pressure, pressure at the site of infusion, and heart rate.

4. A system according to claim 1, wherein the monitor provides one or more features selected from the group consisting of memory/recall function, printout capability, calibration means, fail safe mechanisms, patient thermal indicator, reset button, and a power indicator.

5. A system according to claim 1, wherein the syringe and sensor are adapted to be coupled at the time of use.

6. A system according to claim 1, wherein the sensor is provided with one or more features that couple and/or lock the sensor to the syringe in a removable, semi-permanent, or permanent manner.

7. A system according to claim 6, wherein the coupled sensor is communicably associated with the monitor by a communication link selected from the group consisting of wired and wireless links.

8. A system according to claim 1, wherein the syringe contains a fluid to be delivered.

9. A system according to claim 8, wherein the fluid comprises magnesium ions, and the syringe assembly is adapted to be manually controlled based upon feedback from the patient regarding thermal sensation.

10. A method of using a system according to claim 8, the method comprising the steps of providing the system of claim 8 and delivering the fluid to a patient in a controlled manner based upon feedback from the patient.

11. A method according to claim 10, wherein the delivery is manually controlled based upon one or more patient indicators selected from the group consisting of thermal sensation, pain, or other physical sensation.

12. A method according to claim 10, wherein the system comprises one or more additional sensors or inputs, not operably coupled to the syringe but providing corresponding additional parameters that are communicably associated with the monitor.

13. A method according to claim 12, wherein the additional parameters comprise biological data selected from the group consisting of temperature, oxygen saturation, respiratory rate, blood pressure, pressure at the site of infusion, and heart rate.

14. A system according to claim 1, comprising the syringe and the one or more sensors operably coupled in a permanent manner, and prefilled with a solution to be delivered.

15. A system according to claim 14, wherein the system comprises one or more additional sensors or inputs, not operably coupled to the syringe but providing corresponding additional parameters that are communicably associated with the monitor, the additional parameters comprise biological data selected from the group consisting of temperature, oxygen saturation, respiratory rate, blood pressure, pressure at the site of infusion, and heart rate.

16. A system according to claim 15, wherein the syringe and sensor are adapted to be coupled at the time of use.

17. A system according to claim 16, wherein the sensor is provided with one or more features that couple and/or lock the sensor to the syringe in a removable, semi-permanent, or permanent manner.

18. A system according to claim 17, wherein the coupled sensor is adapted to be communicably associated with the monitor by communication link selected from the group consisting of wired and wireless links.

19. A system according to claim 1, wherein the syringe contains a fluid to be delivered.

20. A system according to claim 19, wherein the fluid comprises magnesium ions, and the syringe assembly is adapted to be manually controlled based upon feedback from the patient regarding thermal sensation.

* * * * *